United States Patent [19]

Manning et al.

[11] Patent Number: 4,788,985
[45] Date of Patent: Dec. 6, 1988

[54] DEVICE FOR CELL SAMPLING IN A BODY CAVITY

[75] Inventors: Patrick R. Manning, Oakbrook; Donald W. West, Lake Forest, both of Ill.

[73] Assignee: Medtest Corporation, Lake Forest, Ill.

[21] Appl. No.: 121,343

[22] Filed: Nov. 10, 1987

Related U.S. Application Data

[63] Continuation of Ser. No. 640,591, Aug. 14, 1984, abandoned, which is a continuation-in-part of Ser. No. 429,689, Sep. 30, 1982, Pat. No. 4,465,078.

[51] Int. Cl.⁴ .............................................. A61B 10/00
[52] U.S. Cl. ........................................ 128/759; 128/756; 604/3
[58] Field of Search ............... 128/749, 756, 757, 759; 604/1-3, 15

[56] References Cited

U.S. PATENT DOCUMENTS

| | | | |
|---|---|---|---|
| Re. 29,061 | 12/1976 | Bucalo | 604/904 |
| 1,822,566 | 9/1931 | Davies | 604/3 |
| 3,155,091 | 11/1964 | Nissenbaum et al. | 128/759 |
| 3,388,043 | 6/1968 | Ingvorsen | 195/139 |
| 3,450,129 | 6/1969 | Avery et al. | 128/2 |
| 3,519,364 | 7/1970 | Truhan | 604/2 |
| 3,614,245 | 10/1971 | Schwartzmann | 604/2 |
| 3,792,699 | 2/1974 | Tobin et al. | 604/2 |
| 3,796,211 | 3/1974 | Kohl | 128/2 B |
| 3,842,166 | 10/1974 | Bucalo | 424/9 |
| 3,918,435 | 11/1975 | Beall | 604/2 |
| 3,932,223 | 1/1976 | Bucalo | 195/139 |
| 3,979,263 | 9/1976 | Bucalo | 195/103.5 R |
| 4,014,748 | 3/1977 | Spinner et al. | 128/759 |
| 4,150,950 | 4/1979 | Takeguchi et al. | 128/759 |
| 4,157,709 | 6/1979 | Schuster et al. | 128/759 |
| 4,223,093 | 9/1980 | Newman et al. | 435/295 |
| 4,245,653 | 1/1981 | Weaver | 128/756 |
| 4,252,904 | 2/1981 | Nelson et al. | 435/294 |
| 4,286,596 | 9/1981 | Rubinstein | 604/286 |
| 4,415,288 | 11/1983 | Gordon et al. | 604/3 |

FOREIGN PATENT DOCUMENTS

| | | | |
|---|---|---|---|
| 990020 | 6/1976 | Canada | 128/759 |
| 142903 | 7/1903 | Fed. Rep. of Germany | 604/15 |

*Primary Examiner*—Max Hindenburg
*Attorney, Agent, or Firm*—Haight & Hofeldt

[57] ABSTRACT

A simple, inexpensive and accurate device of collecting human cells from a body cavity for cytodiagnosis comprising an absorbent carrier which contains an internal, rupturable fluid sac, a means for rupturing the fluid sac and an absorbent outer covering for collection of the cell sample.

16 Claims, 1 Drawing Sheet

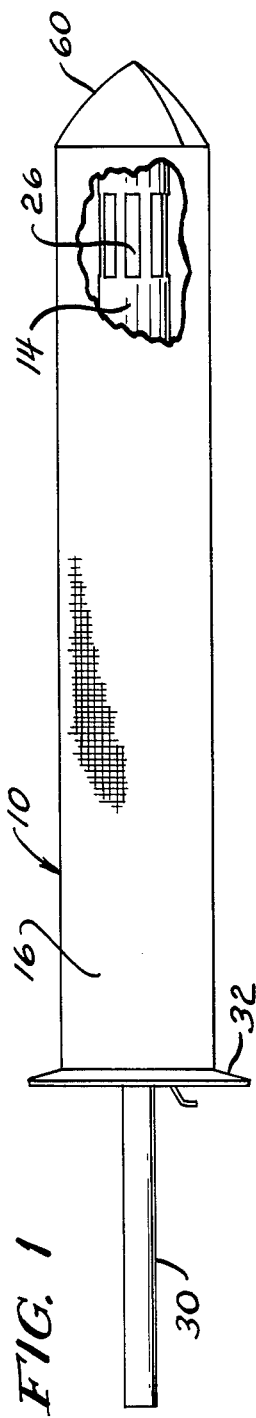
FIG. 1
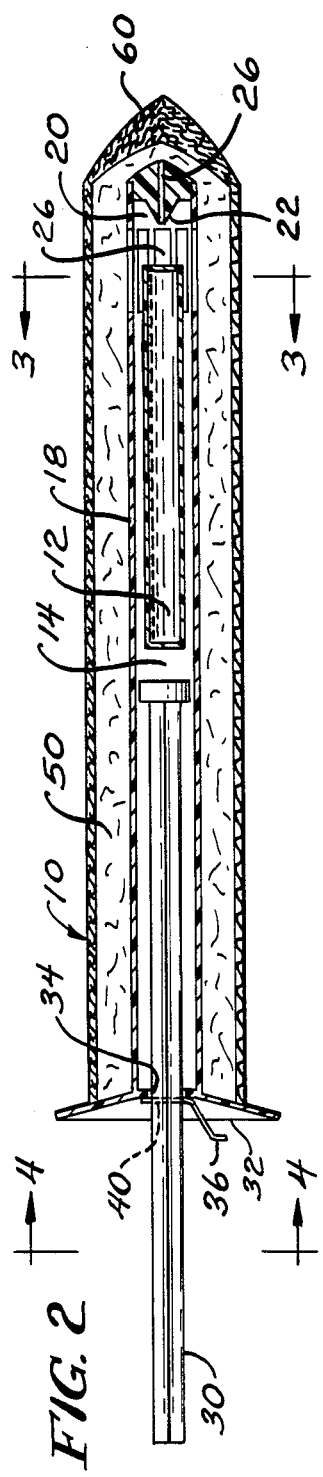
FIG. 2
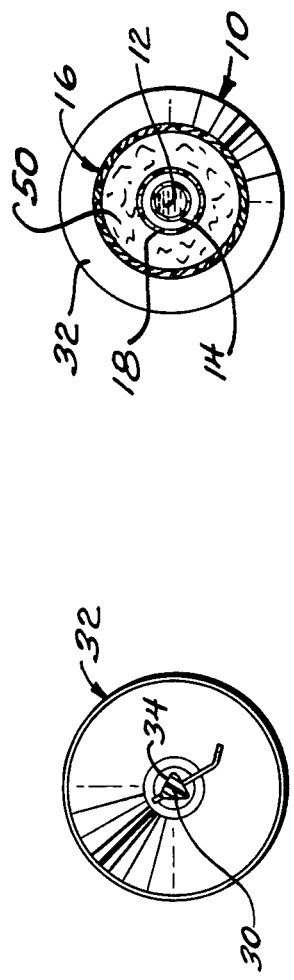
FIG. 3
FIG. 4

DEVICE FOR CELL SAMPLING IN A BODY CAVITY

CROSS REFERENCE

This application is a continuation of U.S. patent application Ser, No. 06/640,591, filed on Aug. 14, 1984 and now abandoned; which was a continuation-in-part of U.S. patent application Ser. No. 06/429,689, filed on Sept. 30, 1982 and issued on Aug. 14, 1984 as U.S. Pat. No. 4,465,078.

BACKGROUND OF THE INVENTION

1. Field of the Invention

This invention relates to a device for collecting human cells from a body cavity for subsequent testing and more particularly to a device which may be used in connection with the self-administered collection of such cells.

2. Description of Prior Art

Since conception by Papanicolaou many years ago, the acceptance and utilization of cytodiagnosis has continued to expand. Today, a number of techniques involving multiple organ systems are available, all derived from the basic concept that comprehensive pathophysiologic changes may be recognized and evaluated as expressed at the cellular level.

Exfoliative cytology ("Pap test") has long been established as a highly accurate diagnostic tool allowing identification of a number of inflammatory, premalignant and malignant states or conditions. It has proven to be a critical technique in the early detection and treatment of lesions of the cervix and vaginal vault.

The simplicity of the procedure and its accuracy have resulted in its routine use by health care personnel and its wide acceptance by the patient population. Currently, the cell sampling is performed by a physician, nurse, or cytotechnologist using an applicator to obtain the appropriate cell sample. The applicator is of such a size and configuration that it cannot be self-administered and requires a trained health care specialist to employ. There are several significant drawbacks with the existing technique and the prior art devices used in connection therewith:

1. The prior art devices require a trained health professional to administer. The time and cost involved thus deprive a significant portion of the population the opportunity of being tested for various pathophysiologic changes and conditions, including cancer.

2. The ability to make a satisfactory slide smear from the sample varies widely as does the expertise of those performing the test.

3. The inclusion of a pelvic examination in a physical examination is becoming less universal as medicine continues in its pattern of specialization. There is a definite trend, particularly in the United States, toward sending patients to a gynecologist for a pelvic exam and eliminating such an exam from the routine office physical.

It would be advantageous, therefore, if a modified cell sampling device were available which would allow self administration, i.e., self sampling, combined with technical uniformity. The time and cost limitations in the use of the Pap test would thus be eliminated.

Accordingly, it is the principal object of the present invention to provide a simple, inexpensive and accurate device for self-administered cell sampling in a body cavity.

It is a further object of the present invention to provide a device which will permit self-administered cell sampling in a body cavity requiring minimal patient instruction.

SUMMARY OF THE INVENTION

In accordance with the subject invention, the foregoing objects have been achieved with an improved device for cell sampling in a body cavity comprising an absorbent carrier which contains an internal, rupturable fluid sac, a means for rupturing the fluid sac and an absorbent outer covering for collection of the cell sample.

The invention may be used in accordance with the method described in applicant's copending U.S. patent application, Ser. No. 429,689, filed Sept. 30, 1982. The carrier is inserted into a body cavity and the fluid sac ruptured. The carrier is then moved or rotated in the body cavity such that a sample of human cells is collected by the carrier from the walls of the body cavity. The carrier is removed and the cell sample transferred for subsequent testing and analysis.

DESCRIPTION OF THE DRAWINGS

FIG. 1 is a side view of the device of this invention.

FIG. 2 is a cut-away view of the device of this invention;

FIG. 3 is a view taken along the line 3—3 of FIG. 2; and

FIG. 4 is a view taken along the line 4—4 of FIG. 2.

DETAILED DESCRIPTION OF THE PREFERRED EMBODIMENTS

Broadly described, the device of this invention comprises an absorbent carrier 10, preferably in a size and configuration enabling the device to be comfortably and conveniently introduced into a body cavity to remain temporarily therein and most preferably in the form and transverse cross-sectional size of a conventional absorbent tampon having a length ranging from about 5 cm to about 18 cm (preferably about 14 cm). The carrier 10 has imbedded therein a rupturable sac 12 containing sterile fluid preferably sterile saline solution. The fluid is provided in an amount sufficient to maintain moistness at the surface of the carrier when released by rupture of the rupturable sac, preferably in an amount ranging from about 0.25 ml to about 3.0 ml and most preferably about 2.0 ml based on use in a carrier having a transverse cross section equal to that of a conventional tampon. An excessive amount of fluid will result in sloughing off of the cell sample at the surface of the carrier. Insufficient fluid will cause the cell sample to dry out prematurely thereby destroying the cell morphology and rendering the sample unusable for subsequent testing and analysis.

In its preferred embodiment, the carrier 10 comprises a channel 14, preferably formed by relatively rigid rubber or plastic tubing 18, which envelops the rupturable sac 12 and protects it from being inadvertently ruptured by radial compression of carrier 10. The longitudinal axis of the channel 14 is located along, and preferably shares, the longitudinal axis of the carrier. The forward end 20 of the channel 14 is enclosed, preferably in such a manner so as to provide an inward directed projection 22 or other means to facilitate rupture of the rupturable sac 12 when desired.

The channel 14 and preferably its forward end 20 are provided with at least one and preferably a plurality of holes or slots 26 through which the sterile fluid from the rupturable sac 12 may pass to the surface of the carrier 10 upon rupture of the rupturable sac 12. The back end of the carrier 10 comprises an end cap 32 rigidly connected to the carrier body 16. In its preferred embodiment, the periphery of the end cap 32 extends beyond that of the carrier body 16 in order to facilitate handling and operation of the device. Through a hole 34 provided in the end cap 32 passes a plunger 30 having a cross section smaller than that of the hole 34 in order to permit substantially non-resistant longitudinal motion of the plunger 30 through the hole 34. In its most preferred embodiment, the cross section of the plunger 30 and the shape of the hole 34 are non-circular with the plunger 30 interacting with the hole 34 so as to permit rotation of the carrier 10 by directly rotating the plunger 30 alone. To prevent operation of the plunger 30 and consequent inadvertant rupture of the rupturable sac 12, a pin 36 is preferentially provided for insertion through a hole 40 in the plunger 30. The hole 40 is located such that the pin 36, when inserted in the hole 40, contacts the end cap 32 thereby preventing further insertion of the plunger 30 and rupture of the rupturable sac 12.

The tubing 18 forming the channel 14 is covered with absorbent material 50, preferably cotton or gauze and most preferably cotton which is then covered with gauze. Applicants have discovered that in this, most preferred embodiment, gauze advantageously collects the cell sample and cotton beneficially maintains the necessary moistness of the absorbent material 50. Applicants have further discovered that insertion of the carrier 10 and collection of cell samples is enhanced by use of a carrier 10 having a forward end 60 of substantially the shape shown in FIG. 1 and FIG. 2 (i.e., substantially parabolic or conical).

Operation of applicants' novel device in its most preferred embodiment is accomplished in substantial accordance with applicants' copending U.S. patent application, Ser. No. 429,689, filed Sept. 30, 1982. Using the periphery of the end cap 32 as a handle and guide, the carrier 10 is inserted into the body cavity. Once the carrier 10 is inserted, the safety pin 36 is removed and the plunger 30 is depressed into and through the channel 14, again using the periphery of the end cap 32 as a handle. The plunger 30 forces the rupturable sac 12 against the projection 22, thereby rupturing the rupturable sac 12 and releasing the saline solution, which passes through the slots 26, moistening the absorbent material 50.

A cell sample is collected on the carrier 10 from the body cavity by rotating the plunger 30 about its longitudinal axis which, in turn rotates the carrier 10 in the body cavity. As the surface of the carrier 10 moves with respect to the body cavity, cells are collected from the walls of the body cavity and retained by the absorbent material 50. Collection is enhanced by the preferred shape of the forward end 60 as shown in FIG. 2. The carrier 10 is removed from the body cavity and transported to a facility for testing and analysis of the collected cell sample. After removal from the body cavity, the cell morphology is preserved by the saline-bearing absorbent material 50.

We claim:

1. Single use apparatus for collecting cells from a body cavity for cytodiagnosis, the apparatus being self-administrable by a user and disposable after analysis of the collected cells, comprising:

an elongated absorbent carrier sized to be substantially completely inserted into the body cavity;
   sterile fluid containing means located in said absorbent carrier to store a predetermined amount of sterile fluid, said containing means having at least a rupturable component;
   protective means associated with said absorbent carrier to prevent said rupturable component from being inadvertently ruptured by radial compression of said absorbent carrier;
   actuating means located at the back end of said absorbent carrier to be operated by the user for causing said rupturable component to be ruptured while said absorbent carrier is substantially completely positioned in the body cavity of the user; and
   an absorbent outer covering on said absorbent carrier for dislodging and retaining cells from the surface of the body cavity of the user, rupture of said containing means releasing sterile fluid to moisten said absorbent outer covering to aid in collecting and preserving a cell sample.

2. The apparatus of claim 1 wherein the sterile fluid is sterile saline.

3. The apparatus of claim 1 wherein said sterile fluid containing means comprises a rupturable sac sized to contain therein sterile fluid in an amount ranging from about 0.25 ml to about 3.0 ml., and said carrier with said covering is sized to substantially lie within the human female cervix and vaginal vault.

4. The apparatus of claim 1 wherein the absorbent outer covering comprises gauze or cotton.

5. The apparatus of claim 4 wherein the absorbent outer covering comprises cotton covered with gauze.

6. The apparatus of claim 1 wherein said sterile fluid containing means is a rupturable sac, and said absorbent carrier includes a channel for containing said rupturable sac, the channel sharing a substantially common longitudinal axis the said absorbent carrier and having a length less than that of said carrier.

7. The apparatus of claim 6 wherein said protective means comprises a substantially rigid tube mounted in the interior of said absorbent carrier, and wherein said tube defines said channel and is provided with means for fluid communication between said channel and said absorbent outer covering.

8. The apparatus of claim 6 wherein said actuating means for rupturing said rupturable sac comprises a plunger which is capable of longitudinal motion in the interior of said channel and which is capable of compressing said rupturable sac.

9. The apparatus of claim 8 and further comprising an end cap rigidly attached to the back end of said absorbent carrier and having a hole therein, the hole being in communication with the channel and being capable of slidably holding said plunger.

10. The apparatus of claim 9 wherein said plunger and the hole have a non-circular cross section and said plunger is engageable with said end cap upon rotation of said plunger, thereby permitting rotation of said absorbent carrier upon rotation of said plunger.

11. The apparatus of claim 9 wherein the outer periphery of said end cap extends beyond the outer periphery of said absorbent carrier.

12. The apparatus of claim 9 wherein said actuating means for rupturing said rupturable sac includes means carried by said plunger for preventing rupture of said rupturable sac by inadvertant actuation of said plunger.

13. The apparatus of claim 6 wherein said actuating means for rupturing said rupturable sac comprises a projection forming a part of said absorbent carrier, said projection being directed into the interior of said channel.

14. The apparatus of claim 13 wherein the means for rupturing the rupturable sac further comprises a plunger capable of longitudinal motion in the channel and capable of compressing and thereby rupturing the rupturable sac against the projection.

15. The apparatus of claim 1 wherein the absorbent carrier has a substantially parabolic or conical forward end.

16. The apparatus of claim 1 and further comprising means for rotating said absorbent carrier about its longitudinal axis after sterile fluid has been released form said sterile fluid containing means.

* * * * *